United States Patent [19]
Carosella et al.

[11] Patent Number: 4,719,107
[45] Date of Patent: Jan. 12, 1988

[54] IMMUNOMODULATING MEDICATION BASED ON FC FRAGMENTS OF HUMAN IGG

[75] Inventors: Edgardo D. Carosella, Lyons; Jacques B. Armand, St Germain, both of France

[73] Assignee: Institut Merieux, Lyons, France

[21] Appl. No.: 679,445

[22] Filed: Dec. 7, 1984

[30] Foreign Application Priority Data

Dec. 7, 1983 [FR] France .................. 83 19568

[51] Int. Cl.$^4$ .................. A61K 39/395; C07K 15/00
[52] U.S. Cl. .................. 424/85; 424/101; 514/21; 530/387; 530/388
[58] Field of Search .................. 260/112 B; 424/101, 424/85; 514/21; 530/388, 387

[56] References Cited

U.S. PATENT DOCUMENTS

| | | | |
|---|---|---|---|
| 4,137,222 | 1/1979 | Makula et al. | 530/387 X |
| 4,465,670 | 8/1984 | Sugisaki et al. | 424/101 X |
| 4,479,934 | 10/1984 | Sedlacek et al. | 424/85 |
| 4,544,640 | 10/1985 | Soma et al. | 530/388 X |

OTHER PUBLICATIONS

Biochemical Journal, 73 (1959), pp. 119–126, Porter.
Journal of Immunology, 122 (1979), 89–96, Berman et al.
Journal of Experimental Medicine, 146 (1977), 241–256, Berman et al.
Journal of Experimental Medicine, 153 (1981), 1161–1172, Morgan et al.
J. Clin. Invest. 67 (1981), 867–877, Durandy et al.
Morgan et al, J. Exp. Med. 154, 1981, 778–790.
Morgan et al, J. Exp. Med. 152, 1980, 113–121.
Barandun et al, Vox Sang. 7, 157–174 (1962).
Sgouris et al, Vox Sang. 13, 71–84 (1967).
Barandun et al, Vox Sang. 28, 157–175 (1975).
Clinical Applications of Immunoglobulin, Edited by P. Lattman, Sandoz Products (1982), pp. 16–27 and 34–35, Barandun et al.
Transplantation, 34, No. 2 (1982), 90–93, Sugisaki et al.
Int. Archs. Allergy Appl. Immun. 57, 375–378 (1978), Skvaril et al.

*Primary Examiner*—Howard E. Schain
*Attorney, Agent, or Firm*—Cushman, Darby & Cushman

[57] ABSTRACT

This medication consists of Fc fragments of human IgG, or of analogues of said fragments, and [is characterized by the fact] that it is free of intact IgG and/or Fab fragments or contains no more than 2% by weight of the latter with respect to total weight (Fc+Fab+IgG), it being understood that said analogues of Fc fragments of human IgG are all fragments or subfragments of Fc and all synthetic or semisynthetic peptides containing peptide sequences present in the Fc fragment, as well as all derivatives of these fragments, subfragments, or peptides, provided that these fragments, subfragments, peptides, or derivatives fulfill the following conditions:

- they have properties that activate the differentiation of suppressive cells;
- they have properties that inhibit antibody-dependent cytotoxicity;
- they do not have properties that activate NK cells.

4 Claims, No Drawings

IMMUNOMODULATING MEDICATION BASED ON FC FRAGMENTS OF HUMAN IGG

The object of the present invention is a new immunomodulating medication based on Fc fragments of human G immunoglobulin. This medication is used particularly in the treatment of immunary dysfunction, including autoimmune diseases, and as an agent for inhibiting transplant rejections in the treatment of patients who must undergo, or have undergone, organ transplants.

Organ transplants, particularly those involving kidneys and marrow, are widespread today. Despite progress in our knowledge of the major histocompatibility system, it is still necessary artificially to inhibit the immune response in order to counter the organism's attempt to destroy the foreign cells of the transplanted organ.

In order to obtain such an inhibition of the immune defenses, various methods—based particularly on the use of complete radiation, chemical therapies (alkylation agents, analogues with puric bases), certain antibiotics, and antilymphocyte serum—are generally used in combination.

It is well known that these methods of inhibiting immunity all have various drawbacks. In particular, they paralyze not only the organism's natural defenses against the transplant, but also those that fight infectious agents such as viruses and germs. Patients are thus left helpless against injection, and very restrictive precautions must be taken in order to avoid it.

The object of the present invention is a medication that inhibits immunological defense responses against the transplanted organ but does not inhibit, indeed even increases, fluid immune defense reactions, which are known to play an essential role in the fight against infections.

The active principle of the medication of the invention consists of the Fc fragment of human G immunoglobulins or its analogues.

It is known that immunoglobulins (abbreviated Ig) are proteins that can be broken down into various categories according to various criteria: IgG, IgM, IgA, IgD, and IgE.

Like the other immunoglobulins, IgG, which is the predominant immunoglobulin in serum, has a multicatenary structure. Various cleavage reactions, particularly enzymatic ones, have made it possible to isolate fragments of this protein.

Thus it is that through hydrolysis with papain or plasmin, the IgG molecule yields three fragments. Two fragments each have an antibody site. These are called Fab fragments. One has no antibody site but does have a number of effector functions. This is called the Fc fragment.

The methods of obtaining the Fc fragment or analogous fragments using enzymatic cleavage with papain, plasmin, etc., are well known. They have been described, for example, by R. R. Porter, *Biochem. J.*, 73 (1959), p. 119.

Unless otherwise indicated, the expression "Fc fragment" used alone will designate Fc fragments of human IgG.

The pharmacological properties of Fc fragments and their role in the various mechanisms of immune defenses, have not been well known up to the present time. Research on an animal model does not make it possible to draw conclusions about activity in other species, since, as we know, the immunoglobulins (and IgG in particular) differ from species to species, and a given immunoglobulin has different effects on the immune response of different species.

Numerous publications have pointed out that the Fc fragments of various immunoglobulins have a stimulating effect on the proliferative response and on the polyclonal activation of human and murin lymphocytes whether or not antigens are present. On the other hand, the Fc fragment of goat immunoglobulins has only a weak mitogenic effect on the lymphocytes of the mouse, while the Fc fragment of rabbit or goose immunoglobulins has no stimulating effect, regardless of the dose. See, for example, M. A. Berman et al., *The Journal of Experimental Medicine*, 146, (1977), pp. 241-256, amd *The Journal of Immunology*, 122, (1979), 89-96.

It is also known that the Fc fragment of human myeloma produces an increase in the proliferation of mouse lymphocytes in the mixed lymphocyte reaction. See, for example, E. L. Morgan et al., *J. Exp. Med.*, 153, (1981), pp. 1161-72.

Likewise, it is known that Fc fragments and human IgG (like intact IgG) have the effect of inhibiting antibody-dependent cell-mediated cytotoxicity (ADCC). see, for example, Wisloff et al., *Scand. J. of Immunol.*, 3 (1974) pp. 29-38.

Finally, it is known that human NK (natural killer) cells, which occur in certain immune reactions, carry receptors for the Fc fragment of IgG, but that the cytotoxic action of the NK cells is not connected to this receptor. See M. E. Neville, *Journal of Immunol.*, 125 (1980), p. 2604.

Given the complexity of the immune defense system and the multiplicity of the phenomena of immunary regulation, and in light of current knowledge in the area of immunology, an active substance can be produced for use as an immunomodulating medication only after all of the effects of the active substances on the various fluid and cell immune reactions, and particularly on the activation or inhibition of cytotoxic or suppressive cells, have been explored. Furthermore, such exploration must necessarily be conducted using an isologic model, without which it is absolutely impossible to foresee any activity of the substance as a medication, for the reasons set out above.

Research on the properties of the Fc fragment of human IgG, using an isologic model, has now revealed interesting pharmacological properties that enable this fragment to be recommended for use as an immunomodulating medication. These properties will make it possible, inter alia, to treat autoimmune diseases and to avoid or to diminish in effect reactions of rejection of transplanted organs.

Fc fragments of human IgG, which stimulate the lymphocytic response, have no effect on the primary allogenic reaction. On the other hand, Fab fragments and intact IgG have an inhibiting effect on the primary allogenic reaction and no effect on the proliferative response.

The Fc fragment of human IgG, like the Fab fragment and intact IgG, has neither a stimulating nor an inhibiting effect on the lymphocytic response in the presence of antigens.

Fc fragments of human IgG have neither a stimulating nor inhibiting effect on the phenomenon of generation of cytotoxic cells in the primary mixed lumphocytic reaction (CML I). However, it has been discovered that Fc fragments have an inhibiting effect on cytotoxicity in the secondary mixed lymphocytary reaction (CML II), as do intact IgG and Fab fragments.

The discovery of this latter property has led to research on the possible influence of the Fc fragment on the stimulation or proliferation of suppressive cells, and the research reproduced hereinafter in the experimental portion of this description shows that Fc fragments of human IgG encourage the development of suppressive lymphocytes and assist in stimulation of presuppressive cells.

Finally, the study of the influence of Fc fragments on the production of whole immunoglobulins in a mitogenic type reaction has made it possible to show an increase in the production of whole immunoglobulins, whereas Fab is inactive and intact IgG leads to an inhibition of the production of total immunoglobulins. See A. Durandy et al., *J. Clin. Invest.*, 67 (March 1981), pp. 867–77.

It should be noted that in the inhibition of antibody-dependent cytotoxic action (ADCC), and in the differentiation of suppressive cells, an effect proportional to the dose of the product studied can be observed. This allows one to suppose that the Fc fragment acts directly on certain T lymphocyte subpopulations.

These various properties of Fc fragments of human IgG thus make it possible to use them as immunomodulating medications that will inhibit cellular immunity while encouraging fluid immunity, and that can therefore be advantageously used in the treatment of patients receiving organ transplant or those suffering from immunary dysfunctions, particularly autoimmune diseases.

Immunomodulating medication, characterized by the fact that its active ingredient consists of Fc fragments of human IgG or of the analogues of said fragments, and by the fact that it is free of intact IgG and/or Fab fragments or contains no more than 2% by weight of the latter with respect to total weight (Fc+Fab+IgG), it being understood that said analogues of Fc fragments of human IgG are all fragments or subfragments of Fc and all synthetic or semisynthetic peptides containing peptide sequences present in the Fc fragment, as well as all derivatives of these fragments, subfragments, or peptides, provided that these fragments, subfragments, peptides, or derivatives fulfill the following conditions:

they have properties that activate the differentiation of suppressive cells;

they have properties that inhibit antibody-dependent cytotoxicity;

they do not have properties that activate NK cells.

The expression "analogues of Fc fragments of human IgG" used in this application covers all fragments or subfragments of Fc, and all synthetic and semisynthetic peptides containing peptide sequences present in the Fc fragment, provided that these fragments, subfragments, peptides, or derivatives satisfy the following conditions:

they have properties that activate the differentiation of suppressive cells;

they have properties that inhibit antibody-dependent cytotoxicity;

they do not have properties that activate NK cells.

The medication of the invention may be administered orally, intravenously, or intramuscularly. To this end, it is produced especially in the form of capsules, tablets, pills, injectable solutions, or lyophilized powder for injectable solutions.

For oral administration, the pharmaceutical form must include an acid-resistant coating allowing the medication to pass through the stomach barrier.

In cases of organ transplant, the medication of the invention may be administered by various methods depending on the techniques of immune suppression used by the doctor before and after the transplant.

The medication of the invention may be administered before the organ transplant to decrease the transplant immunity, or after the transplant, in alternation or together with other immunosuppressive medications. Consideration must be given to the fact that the immunomodulating effect of the medication of the invention is generally obtained only after 6 to 10 days.

Dosology depends notably on the method of administration and on the phase of treatment. It generally varies from 1 mg to 10 g of active ingredient daily in adults. For example, intravenously, the dose of Fc fragment may vary from 1 g to 10 g daily for an adult.

Another object of the invention is the use of the Fc fragment of human IgG or its analogues in the preparation of an immunomodulating medication capable particularly of treating autoimmune diseases and preventing rejection responses, or of reducing their effects, in patients who must undergo or who have undergone organ transplants. Such use includes putting the product into a suitable pharmaceutical form using the usual methods.

Of course, the medication of the invention may be used in combination with other immunodepressive or corticoidal medications.

The following examples illustrate the invention non-limitatively.

The following abbreviations are used in the examples:

ADCC: antibody-dependent cell-mediated cytotoxicity
BSA: bovine serum albumin
CML: lymphocyte-mediated cytotoxicity
F(ab')2: fragment obtained through cleavage of IgG with pepsin
GRP: red chicken corpuscles
Haplotype DR: D-related determinant of the HLA system
HLA Dr, HLA A, B, HLA D: antigenic determinants of the human leucocytic histocompatibility system
Ig: immunoglobulin
MLR: mixed lymphocytic reaction
PBS: phosphate buffer solution
PHA-M: phytohemagglutinin-M
PWM: pokeweed mitogen
SVF: fetal calf serum
SrAB: AB serum

EXAMPLE 1: PHARMACOLOGICAL PROPERTIES OF THE Fc FRAGMENT OF HUMAN IMMUNOGLOBULINS

I. Lymphocytic Proliferation

Search for lymphocytic proliferative action of IgG and Fc and Fab fragments of IgG.

Equipment and Method

1. Preparation of various lymphocytic populations
   a. Obtaining the lymphocytes
   Lymphocytes from peripheral veinous blood of 60 voluntary blood donors were separated on a Ficoll-radioselectan gradient (d: 1077) using A. Boyum's technique (*Scand. J. Clin. Lab. Invest. Suppl.* 97, 21 (1968), p. 1).

b. Obtaining a macrophage-enriched lymphocyte population

The monocytes were separated from a previously obtained lymphocyte population on a Percoll gradient (d: 1064) using the technique of Ulmer and Flad (*J. Immunol. Methods*, 30 (1979), p. 1).

c. Obtaining lymphocytes depleted of adhesive cells

The previously obtained (a) population of lymphocytes was incubated for one hour at 37° C. in a Falcon flask. Nonadhesive cells were recovered.

These three types (a, b, c) of cell populations were kept at −260° C. and thawed at the moment of the test.

d. Peroxydase reaction

The percentage of monocytes in each lymphocyte population was determined by the combined peroxydase reaction according to SATO (Applied Biology Treaty, 1964, vol. 3, p. 95) on a total count of 400 cells per smear for each individual.

2. Fc-Fab fragments and IgG

The various subfragments were prepared using known methods, starting with a human plasma IgG treated with plasmin. The IgG (PRC) was of the $\gamma 1$ type (30%) and the $\gamma 2$ type (70%). The Fab showed a contamination of 4.1% Fc. On the other hand, the Fc was pure.

3. Placement in culture a. The test of lymphocytic transformation was performed on round-bottomed microsheets (96 dishes per sheet) with RPMI to which 20% decomplemented autologous serum was added.

Within each dish were placed 200,000 cells under 150 $\mu l$ of RMPI with 20% autologous serum and 50 $\mu l$ of Fc, Fab, IgC, or PWM (Gibco) diluted in RPMI. Each dilution of each fragment was tested in triplicate.

b. Incubation: The discs were incubated for six days in a humidity-saturated incubator at 37° having an atmosphere of 5% $CO_2$ and 95% air.

c. Marking with tritiated thymidine: At the 144th hour, one microcurie of tritiated thymidine was added to each dish. Incorporation was stopped after 16–18 hours by cooling at +4° C.

d. Precipitation: The cells were collected by precipitation on a Skatron and counted on a beta counter using a scintillation solution.

Results

Of 60 individual tested, 43.4% were high responders (greater than or equal to 10,000 cpm), 18.3% were low responders (less than 10,000 cpm), and 38.3% were nonresponders (less than or equal to 2,000 cpm).

The criterion of high or low responder was set up according to the proliferative response for the cell culture with the Fc fragment (table 1).

The percentage of positive peroxydase cells was 32% in the three groups. On the other hand, in the population of lymphocytes depleted of adhesive cells, it was 1 to 2%. The Fc, Fab, and IgG fragments were tested at 6, 12, and 24 g per culture; 50 and 100 $\mu g$ do not show significant differences from the preceding group (D—N—S).

The results are summarized in table 1.

Conclusions

These tests show evidence of the stimulating effect of the Fc fragment in the lymphocytic proliferative response, compared to the Fab fragment or whole IgG, and of the indispensable presence of the macrophages necessary for this action. These results should be compared with the work done by Weigle on mouse lymphocytes (*J. Exp. Med.*, 146 (1977), p. 241) in which the maximum proliferative response came at five days at with 10 g per culture. Similarly, the depletion of adhesive cells entails an absence of a proliferative response for mouse lymphocytes (*J. Exp. Med.*, 150 (1979), p. 256).

II. Allogenic Lymphocytic Proliferation

Search for inducive or inhibiting action of whole IgG and of Fc and Fab fragments of IgG in the primary allogenic proliferative response.

Equipment and method

The techniques for separating lymphocytes and monocytes and for obtaining the various fragments were described above.

Obtaining T lymphocytes

T lymphocytes were separated on a column of nylon fibers (using the techniques of M. Julius et al., *Eur. J. Immunol.*, 3 (1973), p. 645). Forty million lymphocytes were incubated for 30 minutes at 37° C. with 0.6 g of nylon fibers in a 10 ml syringe.

The nonadhesive cells were recovered. Color controls for peroxydases and E rosettes were done to confirm T lymphocytes enrichment.

These cells were used as responder cells in the mixed culture.

Recovery of supernatants in lymphocyte cultures in the presence of various Ig fragments (Vol. 128, p. 590)

Using the technique of Marylin Thoman (*J. Immunol.*, 1982) monocyte-enriched ($1 \times 10^6$/ml) lymphocytes were incubated for 24 hours at 37° C. in a medium of RPMI 1640—20% SrAB with 60 g of Fc, Fab, or Ig. After 24 hours, the supernatants were recovered by centrifugation.

Mixed lymphocyte culture

The responder cells (nonadhesive cells) were counted and adjusted to a concentration of $1 \times 10^6$/ml. The stimulator cells (total lymphocyte population of monocyte-enriched lymphocytes) were treated with 25 $\mu g$ of mitomycine C per ml and per million cells (using Bach's technique, *Science*, 153 (1966), p. 545) for 30 minutes at 37° C.

Following this treatment, the cells were washed twice with RPMI 10% SrAB. The cell suspension was adjusted to various concentrations: $1 \times 10^6$/ml, $12 \times 10^4$/ml, $6 \times 10^4$/ml, and $3 \times 10^4$/ml.

The stimulator and responder cells were placed in cone-bottomed microsheets using a Hamilton syringe in proportions of 0.05 ml responder cells, 0.05 ml of stimulator cells, and 0.05 RPMI 20% SrAB.

The microsheets were incubated for five days in an incubator set at 37° C.—5% $CO_2$. At the 96th hour, 2 $\mu Cu$ of tritiated thymidine were added to each dish for 18 hours. The cultures were collected by precipitation on Flow filters using a Skatron microprecipitator. After drying, each filter was placed in a plastic tube. Three ml of scintillation solution were added to each tube and counted in a liquid scintillation counter. The results were expressed in counts per minute (cpm).

Results

MLR and F, Fab, and Ig at different concentrations

The various fragments Fc, Fab, Ig at the various concentrations were added to a MLR I.

The Fc fragment at various concentrations (12, 25, 50, and 100 g/culture) had no inducing or inhibiting effect on the MLR I in comparison with RPMI.

On the other hand, the Fab fragment at a concentration of 100 g per culture inhibited the MLR I. IgG at concentrations of 50 and 100 μg entailed an inhibition of MLR I.

Fc, Fab, and IgG in a MLR with various concentrations of stimulator cells

This operation was performed to show evidence of the effect of various fragments under conditions that are suboptimal for the proliferative response. No significant difference was observed in comparison with RPMI. Only IgG at a concentration of 50 μg produced inhibition of MLR I.

Fc, Fab, and Ig in a MLF with monocyte-enriched stimulator cells

Given that the activation of T lymphocytes through induction of Fc fragment occurs through the macrophages, an attempt was made to move the experiment into a more propitious system, retaining suboptimal culture conditions. No inducing effect was observed at the various doses tested. An inhibiting effect was noted for IgG at 24 μg/culture.

MLR and supernatants of cells incubated with Fc, Fab, or Ig

Since the proliferative response is triggered in the first few hours following contact between stimulator cells and responder cells, and since the production of Fc subfragments by the macrophages takes place during the first 24 hours, the supernatants from monocyte-enriched lymphocytes were added to a MLR and incubated for 24 hours at 37° C. with the various fragments.

These supernatants were prepared from autologous cells of the responder cell and tested in a MLR I under optimal and suboptimal proliferation conditions.

No inhibiting or inducing effect was observed with the Fc of Fab fragments or with Ig.

Conclusion

With the Fc fragment, no significant inducive or inhibiting action on human lymphocytes were observed in concentrations of 6, 12, 24, 50, and 100 μg per 50,000 cells in the primary allogenic lymphocytic reaction. The choice of the doses used was made upon evidence of the proliferative action of the Fc fragment on lymphocytes (protocol I, above).

On the other hand, whole immunoglobulin and Fab fragment produce an inhibition of the primary allogenic response in all of the models tested.

III. Effect on Cytotoxic Lymphocytes (CML I and CML II)

Exploration of the effect of Fc and Fab fragments, and of IgG, on the various types of cytotoxicity.

Equipment and methods

The techniques for separating lymphocytes of peripheral blood from voluntary donors and for obtaining the various fragments were described above.

Fc, Fab, and IgG

Placental gamma digested in plasma.

IgG subclasses:
IgG1=57%
IgG2=39%
IgG3=0.2%
IgG4=3.7%

Antibody-dependent cell-mediated cytotoxicity (ADCC)

The technique used is that described by F. Wisloff, T. E. Michaelsen, and S. S. Froland, Scand. J. Immunol., 3 (1974), pp. 29–38).

The target cells are GRPs sensitized with anti-GRP rabbit IgG and marked with chrome 51.

ADCC test

The effector cells (lymphocytes of peripheral blood) were counted and adjusted to a concentration of $5\times10^6$/ml in RPMI 10% SVF.

Using a Hamilton syringe, 100 μl of effector cells [and ] 50 μl of substances to be triple tested at different dilutions were placed in round-bottomed microsheets.

Following 20 min of incubation at 37° C. 50 μl of sensitized and marked GRP was distributed, giving a final ratio of 50 effector cells for every target cell (50:1).

Spontaneous salting out was determined by incubating the GRPs in a medium of RPMI 10% SVF; maximum salting out was determined by adding 1N hydrochloric acid to the GRPs. As evidence of the activity of the antiserum, the effector cells were placed opposite GRPs preincubated with normal rabbit serum.

Following 18 hours of incubation at 37° C. in a 5% $CO_2$ humid atmosphere, the sheets were centrifuged for 10 min at 800 rpm. The supernatants were recovered on tampon filters (Flow, Ref. 78-21-005).

"Natural killer" (NK) cytotoxicity

The technique used is that described by B. M. Vose, F. Wanky, S. Argov, and E. Klein, Eur. J. Immunol., 7 (1977), pp. 753–57).

The target cells were K562 cells (human myeloid line) marked with chrome 51.

NK test

The effector cells (lymphocytes of peripheral blood) were adjusted to a concentration of $5\times10^6$/ml, $2.5\times10^6$/ml, $1.2\times10^6$/ml, and $6\times10^5$/ml.

The methodology of their treatment and distribution was identical to that used for the ADCC. The target cells were distributed under 50 μl, yielding a final ratio of 50 effector cells to one target (50:1, 25:1, 12:1, and 6:1). Spontaneous and maximum salting out, and recovery of supernatants, were done under the same conditions as in the ADCC text.

Cytotoxicity with primary lymphocytic mediation (CML I) and secondary lymphocytic mediation (CML II)

This research was done using the method of Lightbody et al., Gen. Bact. Virol. Immunol., 64 (1971), p. 243.

Effector cells

The allogenic sensitization phase involved a mixed culture identical to the one described above (see II, above).

In the two tests, sensitization was performed against a single D r haplotype, taking into account the difference between HLA A, B of the responder and stimulator cells.

Target cells

The stimulator cell that served for the sensitization of the respective MLRs was used as the target cell in the two tests. Stimulated for 72 hours with PHA-M (Gibco), these cells were marked with chrome 51 eighteen hours before the test at a level 200 l per $10\times10^6$ cells.

After successive washings, the cells were counted using trypan blue and adjusted to $200\times10^3$/ml. The CML test was then performed in round-bottomed microsheets. Quantities of 100 l of the effector cells, treated as described previously, were incubated with 50 l of target cells for 4 hours at 37° C. in a humid atmosphere of 5% $CO_2$, yielding a ratio of 50:1 in the case of CML I and 50:1. 25:1, 12:1, and 6:1 in the case of CML II. The spontaneous and maximum salting out, as well as the recovery of the supernatants, were performed under the conditions described above. In the four tests of cytotoxicity, the salting out of chrome 51 was measured on a gamma counter for 2 min. The results were expressed in percentage of cytotoxicity in accordance with the formula:

Percentage salting out of Cr 51 =

$$\frac{\text{cpm test salting out} - \text{cpm spontaneous salting out}}{\text{cpm maximum salting out} - \text{cpm spontaneous salting out}} \times 100$$

Any cytotoxicity greater than 10% is considered positive.

Results

Antibody-dependent cytotoxicity

Inhibition of antibody-dependent cytotoxicity with Fc fragment and with Ig was observed in all of the individuals tested. This inhibition increases in direct proportion to the concentration of Fc fragment or of IgG (table 2).

Inhibition of killer activity was revealed to be even greater with Fc fragment than with IgG, with 6 µg of Fc yielding an inhibition equal to 50 µg of Ig.

On the other hand, no inhibiting effect was observed with Fab, even at very high doses.

"Natural killer" action

It was not possible to gain evidence of any inhibition of NK activity with the Fc-Fab fragments or Ig, even at very sizable doses. To confirm these results at two extreme doses (6 µg and 100 µg) NK activity was tested with different ratios of effector and target cells. No significant difference, at any dose or ratio, was observed (table 3).

Primary and secondary cell-mediated cytotoxicity

CML I was not modified by the action of IgG and of Fc and Fab fragments tested at different doses.

On the other hand, CML II was inhibited by Fc and Fab fragments at doses of 25, 50, and 100 µg. IgG showed significant inhibition at all of the doses used (table 4).

IV. Action of Human Fc-Fab Fragments and Ig on the Activity of Suppressive and Presuppressive Cells for Primary Allogenic Response

Purpose

Exploration of the activity of Fc and Fab fragments, and of Ig, on T cells that suppress the allogenic proliferative response and on the differentiation of presuppressive cells.

Equipment and method

The techniques used to separate the lymphocytes of peripheral blood from voluntary donors and to obtain the various fragments were those already described hereinabove.

Placental gamma digested in plasmin. Purity of fragments used (through ACA 44 gel filtration): Fc: 100%, Fab: 94.6%, (5.4% 7S), Ig (PRG) 7S: 95.4% 10S: 2.8% 10S: 1.8%, IgG1: 57%, IgG2: 39%, IgG3: 0.2%, IgG4: 3.7%.

The voluntary blood donors were studied for the principal determinants of the HLA-Dr complex using serology and conventional or modified lymphotoxicity (lymphocytic suspension enriched with B cells).

Allosensitization: M. J. Sheeny, F. H. Bach, *Tissue Antigens*, 8 (1976), pp. 157-71.

For allogenic sensitization in vitro, $10 \times 10^6$ lymphocytes used as responders were placed in the presence of $10 \times 10^6$ mitomycinated allogenic cells, incompatible for Ag HLA-Dr (25 µg/$10^6$ cells/ml), used as stimulators. The culture was made in Falcon bottles (CA 3013) with 20 ml of RPMI 1640 medium with the addition of 10% of a pool of AB serum, for a period of 10 days in a humidified incubator at 37° C. and in the presence of 5% $CO_2$.

Suppression test (J. Dausset, *Nature*, 278 (1978), p. 502).

The suppressive action of in vitro allosensitized lymphocytes was evaluated in a MLR I with three cell populations present: responder lymphocytes, mitomycinated stimulator cells and mitomycinated allosensitive cells (these being autologous with the responder cells).

Counting was performed on a liquid scintillation counter.

The suppression percentage was evaluated according to the formula:

% suppression =

$$1 - \left( \frac{\text{median experimental value } (CPM)}{\text{median control } (CPM)} \right) \times 100$$

Effect of the different fragments on presuppressive and suppressive cells

To obtain evidence of stimulating action by presuppressive cells, two different models were tested.

The first consisted of a one-hour preincubation of whole lymphocytes of peripheral blood with the different fragments of Fc and Fab or with IgG. After several washings, these cells were mitomycinated and placed as tertiary cells in an MLR I under the conditions described above. The control group was preincubated with RPMI.

The second protocol made it possible to obtain evidence of a possible inducive effect on the development of suppressive cells. In the allosensitization step, IGG and the Fc and Fab fragments were added in different doses on day 0. After 10 days of sensitization, these cells were added as tertiary cells into a MLR I under the conditions previously described.

Finally, in order to describe the effect of these fragments on the suppressive cells, different doses of Fc, Fab, and Ig were added in the three-cell test.

Results (table 5)

1. Effect of Fc and Fab fragments and Ig in the preincubation of nonsensitized cells added as tertiary cells In the suppression test, various doses of Fc and Fab fragments and Ig were incubated for an hour with the sensitized cells before being washed and mitomycinated.

The previously incubated cells with the fragment Fc produce an increase in inhibition of the MLR I proportional to the dose of Fc used. This increase is significant for doses of 15 and 30 µg/ml. We also find a significant inhibition of the MLR with preincubated cells in the presence of Ig in doses of 15 µg.

On the other hand, the preincubated cells with the fragment Fab do not show any significant inhibition of the allogenic response.

2. Activity of Fc, Fab fragments and IgG in allosensitization

Various doses of Fc and Fab fragments and intact IgG were added at day 0 of allosensitization.

The sensitized suppressive cells in the presence of the fragment Fc showed an inhibiting effect in the MLR I that was significantly higher than that of the control cells, both at 1.5 μg and at 100 μg per culture. In addition, the cells incubated with intact Ig show a significant increase of inhibition of the MLR I at doses greater than 3 μg. On the other hand, the cells sensitized in the presence of the fragment Fab produce no significant difference.

In cases where the percentage of suppression was very high, it was difficult to evaluate the increase. An additional experiment was performed. Allosensitized and mitomycinated cells were added at various concentrations to produce ratios of 1:1, 2:1, and 4:1 of responder cells to suppressor cells. In this case, we again find a significant increase in suppressive activity at a dilution of 8:1 with cells that have been sensitized in the presence of Fc fragment.

3. Activity of Fc, Fab fragments and Ig in test of the suppression of allogenic response I Different doses of Ig and of Fc and Fab fragments were introduced into the three-cell MLR I at the moment of the test. No inducing or inhibiting activity was observed.

Conclusions

The first indication of the existence of suppressor cells developed in the course of the secondary response came from the observation that cells that had been twice allosensitized against the same alloantigen showed less of a proliferative response than with a single allosensitization. Proof of an active process was obtained by adding these allosensitized and irradiated cells to a classic primary MLR.

The suppressor cells are specific to the HLA-Dr antigen presented by the stimulator cell. They appear as T lymphocytes, since after 10 days of culture, 95% of the allosensitized cells form E rosettes, less than 3% have surface IgG, and less than 2% have monocytes. The suppression mechanism produced by an in vitro allogenic hyperimmunization appears to be quite similar to the multitransfusional process used before a kidney transplant, which leads to improved survival of the transplant, as reported by Opelz and Teroski (*Transplantation*, 29 (1980), p. 153).

The purpose of the experiments described above was to show evidence of activity by IgG and Fc and Fab fragments in the development of presuppressive lymphocytes, and of direct activity on suppressor cells.

V. Production of Whole Immunoglobulins from Fragments Fc, Fab, and from IgG

Purpose

To show evidence of the production of immunoglobulins following stimulation by Fc, Fab, and IgG.

Equipment and methods

1. Preparation of various lymphocyte populations

See above for techniques for separating lymphocytes of peripheral blood from voluntary donors and for obtaining the various subpopulations and fragments. Placental gamma digested in plasmin: see V (sic: IV) above for purity and characteristics.

2. Marking antiserum with iodine 125

Iodine 125 S4 was used to mark F(ab')2 of goat (anti-whole human Ig) (Cappel Laboratories).

The mixture of marked F(ab')2 and excess iodine was deposited on a Sephadex G 50 column. The first peak occurred at F(ab')2 (PM 50,000); the second corresponded to a volume of 8 to 10 ml depending on the results of the marking in 0.5M phosphate buffer pH 7.5. As a protein support, a final 1% of goat serum without gamma-globulin was added.

The marking efficiency was calculated according to the formula:

$$\frac{cpm \text{ peak } F(ab')2}{cpm \text{ peak } F(ab')2 + cpm \text{ excess } I\text{-}125} \times 100$$

Specific activity was calculated as follows:

$$\frac{cpm}{ng \text{ marked } F(ab')2}$$

$$ng \text{ marked } F(ab')2 = 1000 \times \frac{\text{vol. taken test } (\mu l) \times \text{qty } F(ab')2(g)}{\text{final vol. marked } F(ab')2 \,(\mu l)}$$

3. Titration of human IgG: RIA test

After one night at +4° C. for purposes of absorbing the anti-human Ig goat F(ab')2 in interchangeable cups, these cups were suctioned and saturated with PBS+5% BSA for one hour at 37° C.

A. Incubation of substances to be tested

Dilution of standard gamma-globulin

Placental gamma-globulin in a concentration of 60 g/ml was used as a standard. Ten successive ½ in ½ dilutions of this solution in PBS+0.5% BSA, plus 0.05 Tween 20, were performed.

Dilution of substances to be tested

Following six days of culturation of 1×10⁶/ml of peripheral blood cells, nonadhesive cells, and macrophage-enriched cells in RPMI plus 10% SVF and in the presence of Fc, Fab, Ig, or RPMI at 60 g/ml, the supernatants were collected after centrifugation.

They were then used apart, 1/5, 1/25, and 1/125 in PBS 0.5% BSA plus 0.05% Tween 20.

One hundred 1 of each dilution of substance was placed in each of three cups.

These were than incubated for 2 hours at 37° C. and rinsed several times.

B. Contact antigen—anti-human Ig goat F(ab')2 marked with iodine 125

100 μl of marked and diluted F(ab')2 were placed in each cup. After 2 hours of incubation at 37° C. several washings were done with PBS Tween. Each cup was then completely suctioned. The counting was done on a gamma counter.

C. Determination of the quantity of Ig in the supernatants $cpm \text{ real} = cpm(Fc^x + lympho + RPMI \text{ serum}) - cpm(FC + RPMI \text{ serum})$ $x[=]Fc \text{ or } Fab \text{ or } Ig$ These cups were than regressed against the standard.

Results and Conclusions (table 6)

The production of whole immunoglobulins from different lymphocyte subpopulations was significantly higher with fragment Fc than with fragment Fab.

On the other hand, IgG appears to inhibit rather than stimulate the production of whole IgG, compared with the spontaneous production of IgG.

Introducing immunoglobulins and subfragments into the RIA technique makes it necessary to do parallel checks on five-day supernatants without cells in order to obtain comparable results.

This methodology helps in obtaining evidence of the in vitro production of IgG from lymphocytes stimulated with Fc.

EXAMPLE 2: MAKING A PHARMACEUTICAL COMPOSITION

Fc fragments were prepared from purified human IgG using the techniques of J. L. Oncley et coll., *J. of Am. Chem. Soc.*, 71 (1949), p. 541, and treated with human plasmin using the techniques of R. Plan and M. F. Makula, *Vox Sanguinis*, 28 (1975), pp. 157–175. This IgG comes from blood taken from the vein or pressed from placenta. The solution of apyrogenous Fc fragments was sterile filtered, distributed in volumes of 2.5 g of active ingredient per flask, and lyophilized.

At the time of use, the solution is reconstituted with water used for injectable preparations.

[In English in original] In the examples, the separation of fragments Fc and Fab is carried out by salting out (with ammonium sulphate solutions) followed by molecular sieving through column (gel filtration).

TABLE 1

| μg per culture | N° | Fc | Fab | IgG | RPMI | PWM | Responders |
|---|---|---|---|---|---|---|---|
| 6 | 26 | 23308 ± 4507 | 11446 ± 1665 | 10985 ± 1440 | 6930 ± 569 | 66884 ± 4322 | High |
| 12 | 26 | 18324 ± 2026 | 13641 ± 2339 | 13715 ± 2199 | 6930 ± 569 | 66884 ± 4322 | Responders |
| 24 | 26 | 21309 ± 2630 | 15410 ± 5093 | 10024 ± 1463 | 6930 ± 569 | 66884 ± 4322 | 43.4% |
| 6 | 11 | 6161 ± 400 | 8763 ± 631 | 3010 ± 489 | 4100 ± 508 | 47319 ± 6898 | Low |
| 12 | 11 | 7278 ± 948 | 3985 ± 1298 | 3126 ± 593 | 4100 ± 508 | 47319 ± 6898 | Responders |
| 24 | 11 | 8032 ± 671 | 5248 ± 1179 | 5128 ± 567 | 4100 ± 508 | 47319 ± 6898 | 18.3% |
| 6 | 9 | 1385 ± 413 | 1110 ± 349 | 1483 ± 433 | 1689 ± 334 | 37145 ± 4717 | Adhesive |
| 12 | 9 | 1369 ± 471 | 1137 ± 288 | 1064 ± 334 | 1689 ± 334 | 37145 ± 4717 | Cells |
| 24 | 9 | 1435 ± 489 | 1109 ± 244 | 1661 ± 423 | 1689 ± 334 | 37145 ± 4717 | (—) |

Autologous serum peroxydase 32%

TABLE 2

ADCC and fragment Fc, Fab, IgG - Test ADCC 50:1

% cytotoxicity RE1 Cr 51 M ± ES n = 7

| | Prod | | | |
|---|---|---|---|---|
| *CONC | Fc | Fab | IgG | RPMI (control) |
| 7,5 μg | 17 ± 5,6 | 18 ± 4,7 | 20,2 ± 3,48 | 15 ± 2,3 |

TABLE 2-continued

| dose dish | Fc | Fab | IgG | RPMI (Control) |
|---|---|---|---|---|
| **6 μg | 25,2 ± 5,5 >46%* (a) | 46,8 ± 8,2 >0,01 | 33,1 ± 5,8 >30%* | 47,4 ± 7,4 (h) |
| 12 μg | 19,1 ± 4,56 >59%* (b) | 47,9 ± 7,6 0 | 30,6 ± 5,5 >35* (e) | 47,4 ± 7,4 |
| 24 μg | 15,5 ± 3,5 >67%* (c) | 46,4 ± 7 >0,01 | 28,0 ± 5,7 >40%* (f) | 47,4 ± 7,4 |
| 50 μg | 12,3 ± 3 >74%* (d) | 45,0 ± 7,5 >0,04 | 24,6 ± 4,5 >48%* (g) | 47,4 ± 7,4 |

**n = 6; *% inhibition
(a) vs RPMI = $p < 0,025$  (e) vs RPMI = $p < 0,05$
(b) vs RPMI = $p < 0,010$  (f) vs RPMI = $p < 0,05$
(c) vs RPMI = $p < 0.005$  (g) vs RPMI = $p < 0,02$
(d) vs RPMI = $p < 0,005$  (c) vs f = $p < 0,05$
(d) vs g = $p < 0,025$

TABLE 3

NK activity at various concentrations of fragment Fc, Fab, IgG

*M ± ES % Cytotoxicity ( )/dish

| Prod | 6 μg | 12 μg | 24 μg | 100 μg |
|---|---|---|---|---|
| Fc | 39,7 ± 8,9 | 40,0 ± 8,9 | 37,7 ± 8,6 | 39,5 ± 9 |
| Fab | 37,5 ± 7,7 | 40,5 ± 8,8 | 38,7 ± 8,9 | 39,2 ± 8,5 |
| IgG | 33,7 ± 8 | 35,0 ± 8 | 34,2 ± 8,2 | 34,7 ± 8,6 |
| RPMI | 37,5 ± 8,4 | 37,5 ± 8,4 | 37,5 ± 8,4 | 37,5 ± 8,4 | n = 4
*Ratio 50 effector cells to 1 target cell

TABLE 4

CML II
Ratio effector cells to target cells 50:1

% Cytotoxicity M ± ES n = 4

| μg/dish | Fc | Fab | IgG | RPMI n = 7 |
|---|---|---|---|---|
| 6 μg | 20,2 ± 1,5 (k) | 21,0 ± 0,5 | 15,0 ± 1,9 (f) | 24,1 ± 2,6 |
| 12 μg | 21,5 ± 1,75 | 20,2 ± 1,1 | 16,7 ± 1,4 (g) | 24,1 ± 2,6 |
| 25 μg | 16,5 ± 2,3 (a) | 14,0 ± 2,9 (d) | 16,7 ± 1,3 (h) | 24,1 ± 2,6 |
| 50 μg | 16,7 ± 3 (b) | 14,7 ± 2,9 (e) | 15,5 ± 2,3 (i) | 24,1 ± 2,6 |
| 100 μg | 15,5 ± 2,7 (c) | 17,7 ± 3,9 | 12,7 ± 2,1 (j) | 24,1 ± 2,6 |

(a) vs RPMI:$p < 0,025$  (e) vs RPMI:$p < 0,025$  (i) vs RPMI:$p < 0,02$
(b) vs RPMI:$p < 0,050$  (f) vs RPMI:$p < 0,005$  (j) vs RPMI:$p < 0,005$
(c) vs RPMI:$p < 0,025$  (g) vs RPMI:$p < 0,005$  (k) vs f:$p < 0,05$
(d) vs RPMI:$p < 0,025$  (h) vs RPMI:$p < 0,005$

Effector cells (10 J + 2 JR)
BL*:α1 (2/6 α 1/6)   SP*:α1 (7/- 1/7)   GC*:α6 (2/- α 2/6)
ML*:α3 (2/5 α 3/5)   MC*: αND          RP*:ND

TABLE 5

Activity of pre-incubated cells with fragments Fc, Fab and IgG

% SUPP. $\bar{X}$ ± E.S.

TABLE 5-continued

| | | | | |
|---|---|---|---|---|
| n = 10 | | | | |
| 15 μg | 31,2 ± 2,9 (a) | 22 ± 3,8 (c) | 43,5 ± 5,7 (e) | 15 ± 2,3 |
| n = 23 | | | | |
| 30 μg | 46,2 ± 5,9 (b) | 22 ± 3,4 (d) | 22,3 ± 4,2 (f) | 15 ± 2,3 |
| n = 23 | | | | |

*conc/ml/10⁶ lymphocytes (a) vs RPMI:p < 0,005 (b) vs RPMI:p < 0,005 (c) et (d) vs RPMI:p NS (e) vs RPMI:p < 0,005

(f) vs RPMI: p NS

Activity of fragments Fc, Fab, IgG in allosensitization.
Test Suppr. A + B + Fc → A + (ABFc) + B

| | % inhibition $\bar{X}$ ± ES PROD | | | |
|---|---|---|---|---|
| CONC* | Fc | Fab | IgG | RPMI |
| 1,5 μg | 81 ± 2,49 n = 12 | 71 ± 5,4 n = 5 | 72 ± 8,1 n = 9 | 63,7 ± 3,7 |
| 3 μg | 75 ± 5 | 64 ± 7,5 | 76 ± 2,8 | 63,7 ± 3,7 |
| 6 μg | 84 ± 1,5 | 66 ± 2,98 | 90 ± 2,29 | 63,7 ± 3,7 |
| 24 μg | 81 ± 2,76 | 74 ± 3,3 | 89,3 ± 2,82 | 63,7 ± 3,7 |
| 100 μg | 84 ± 1,68 | 64,7 ± 5 | 79 ± 3,7 | 63,7 ± 3,7 |

Dr SC+ = 3/7 α 1/7 DP+ = 1/7 α 5/7 BV+ = 1/7 α 1/- MB+ = 5/- α 1/5 Fc 1, 5, 6, 24, 100 μg vs RPMI:p < 0,005
Fc 3 μg vs RPMI:p = 0,05 IgG 3 μg vs RPMI:p < 0,05
IGg 6, 24, 100 μg vs RPMI:p < 0,005
*Concentration/20000 responder lymphocytes Test of suppression at various
concentrations of suppressive cells

| | D + S→ + Fc D + (DS+)← + S← % Supp $\bar{X}$ ± ES PROD | | | |
|---|---|---|---|---|
| CONC | Fc* | Fab* | IgG* | RPMI |
| 50.000→ | 82 ± 2,1 | 80 ± 1,2 | 74,6 ± 2,1 | 80 ± 1,8 |
| 25.000← | 67 ± 3,9 | 63,5 ± 2,4 | 53,3 ± 5,3 | 61,5 ± 5,5 |
| 12.000← | 61,8 ± 4,4 | 51,3 ± 8,4 | 47 ± 9,6 | 51,6 ± 10 |
| 6.000← | 38 ± 4,8 (a) | 30,6 ± 1,5 | 30,8 ± 7,5 | 24 ± 5,6 (b) |

Dr:3/7 α 7/- n = 6 a vs b:p < 0,025
*1,5 ug/200000 responder lymphocytes

Activity of fragments Fc, Fab, IgG
in test of suppression of allogenic response I

| | | $\bar{X}$ ± ES + supp PROD | | | |
|---|---|---|---|---|---|
| CONC | N° exp | RPMI | Fc | Fab | IgG |
| 6 μg | 8 | 76,7 ± 3 | 75,8 ± 3 | 78,3 ± 3,3 | 70,3 ± 4,62 |
| 12 μg | 13 | 74,4 ± 2,6 | 69,6 ± 3,71 | 74,3 ± 2,61 | 72,7 ± 3,24 |
| 24 μg | 11 | 48,2 ± 4,2 | 64,6 ± 7,4 | 58,3 ± 7,8 | 49,4 ± 4,83 |
| 50 μg | 17 | 54,1 ± 3,9 | 58,4 ± 4,38 | 58,4 ± 4 | 59,2 ± 4,6 |
| 100 μg | 12 | 48,2 ± 4,2 | 59,5 ± 6,56 | 55,1 ± 7,4 | 52,3 ± 5,5 |

TABLE 5-continued

Suppressor cells
SB+: 5/7 B+ 1/7 → α1
BL+: B 2/6 L+ 1/6 → α1
PePi+: P2 7/3 Pi+ 7/5 → α5
6L+: G 5/7 L 2/5 → α2
RP+: R 3/5 P 1/7 → α1 et 7

TABLE 6

Production of whole immunoglobulins from
various lymphocyte sub populations

Percoll lymphocytes

| | Dilution $\bar{X}$ ± ES ng/ml n = 4 ind. | | | | |
|---|---|---|---|---|---|
| Supernatants | Fc | Fab | IgG n = 5 | RPMI | PWM |
| 1/1 | 2700 ± 1300 | 1060 ± 350 | 100 ± 40 | 630 | 1590 ± 887 |
| 1/5 | 256 ± 130 | 350 ± 202 | 58,4 ± 23 | 205 | 2170 ± 1850 |
| 1/25 | 44 ± 29 | 81 ± 42,7 | 47,8 ± 22 | 120 | 135 ± 31 |
| 1/125 | 25,4 ± 15 | 28,2 ± 24 | 42,6 ± 20 | 80 | 42 ± 33 |

NA lymphorytes

| | Dilution $\bar{X}$ ± ES ng/ml n = 7 ind. | | | | |
|---|---|---|---|---|---|
| Supernatants | Fc | Fab | IgG | RPMI | PWM |
| 1/1 | 520 ± 160 | 229 ± 110 | 53 ± 18 | 200 | 1210 ± 1000 |
| 1/5 | 123 ± 63 | 110 ± 47 | 50 ± 20 | 60 | 455 ± 253 |
| 1/25 | 67 ± 24 | 28,1 ± 11,5 | 44 ± 19 | 65 | 11 ± 5 |
| 1/125 | 13 ± 11 | 29,5 ± 10 | 35 ± 16 | 60 | 9,3 ± 2,7 |

Lymphocytes of peripheral blood

| | Dilution $\bar{X}$ ± ES ng/ml n = 4 ind. | | | | |
|---|---|---|---|---|---|
| Supernatants | Fc | Fab | Ig | RPMI | PWM |
| 1/1 | 750 ± 330 | 207 ± 30 | 115 ± 32 | 485 | 2320 ± 183 |
| 1/5 | 132 ± 31 | 96,7 ± 15 | 73,2 ± 10 | 185 | 390 ± 197 |
| 1/25 | 58,2 ± 19 | 65,7 ± 14 | 68,5 ± 16 | 120 | 74 ± 21 |
| 1/125 | 37,2 ± 10 | 44 ± 18 | 51,7 ± 16,9 | 60 | 43 ± 16 |

We claim:

1. A process for the treatment of autoimmune diseases and for the prevention of organ transplant rejections, comprising administering to a human patient having an autoimmune disease or having undergone an organ transplant, an effective amount of an immunomodulating medicine composition comprising a pharmaceutically acceptable carrier and an effective amount of, as the active ingredient, Fc fragments of human IgG, said Fc fragments being free of intact IgG and/or Fab fragments or containing no more than 2 percent by weight of intact IgG and/or Fab fragments with respect to the total weight of Fc+Fab+IgG, and said Fc fragments being characterized in that they (a) activate the differentiation of suppressive cells, (b) inhibit antibody-dependent cytotoxicity and (c) do not acitvate NK cells.

2. The process of claim 1 wherein said Fc fragments of human IgG contain no more than 1 percent by weight of intact IgG and/or Fab fragments.

3. The process of claim 1 wherein said Fc fragments of human IgG are free of intact IgG and/or Fab fragments.

4. A process for the prevention of organ transplant rejections comprising administering to a human patient having undergone an organ transplant, an effective amount of an immunomodulating medicine composition comprising a pharmaceutically acceptable carrier and an effective amount of, as the active ingredient, Fc fragments of human IgG, said Fc fragments being free of intact IgG and/or Fab fragments or containing no more than 2 percent by weight of intact IgG and/or Fab fragments with respect to the total weight of Fc+Fab+IgG, and said Fc fragments being characterized in that they (a) activate the differentiation of suppressive cells, (b) inhibit antibody-dependent cytotoxicity, and (c) do not activate NK cells.

* * * * *